(12) United States Patent
Perricaudet et al.

(10) Patent No.: US 6,696,420 B1
(45) Date of Patent: Feb. 24, 2004

(54) ADENOVIRAL VECTOR WITH A DELETION IN THE E1A CODING REGION EXPRESSING A HETOROLOGOUS PROTEIN

(75) Inventors: Michel Perricaudet, Paris (FR); Annick Ballay, Orgeval (FR); Massimo Levredo, Roma (FR); Pierre Tiollais, Paris (FR)

(73) Assignees: Institut Pasteur, Paris (FR); Centre National de la Recherche Scientifique, Paris (FR); Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 08/093,901

(22) Filed: Jul. 20, 1993

Related U.S. Application Data

(63) Continuation of application No. 07/935,459, filed on Aug. 26, 1992, now abandoned, which is a continuation of application No. 07/790,080, filed on Nov. 13, 1991, now abandoned, which is a continuation of application No. 07/456,200, filed on Dec. 20, 1989, now abandoned, which is a continuation of application No. 07/293,556, filed on Jan. 5, 1989, now abandoned, which is a continuation of application No. 06/799,938, filed on Nov. 20, 1985, now abandoned.

(30) Foreign Application Priority Data

Nov. 20, 1984 (FR) .............................. 84 17674

(51) Int. Cl.$^7$ .......................... A61K 48/00; A61K 35/00
(52) U.S. Cl. ........................ 514/44; 424/93.1; 424/93.2; 424/93.21
(58) Field of Search .............................. 514/44; 424/89, 424/93 A, 93 T, 93.1, 93.2, 184.1, 93.6, 93.21

(56) References Cited

U.S. PATENT DOCUMENTS 4,920,209 A * 4/1990 Davis et al. ................ 435/235

FOREIGN PATENT DOCUMENTS

| EP | 0 086 707 | 8/1983 |
| EP | A2 0 086 707 | 8/1983 |
| WO | WO 83/0293 | 7/1983 |
| WO | A1 WO 83/0239 | 7/1983 |
| WO | 8302393 | 7/1983 |

OTHER PUBLICATIONS

Osborne etal. (1982) Cel 29: 139–48.*
Laub et al. (1983) J. Virology 48: 271–80.*
Kruczet et al. (1983) PNAS 80: 7586–90.*
Gluzman et al. (1982) in Eukaryotic Viral Vectors, Cold Spring Harbor Labs., ed. Gluzman, pp. 187–92.*
Kruczek et al. (1983) Proc. Natl. Acad. Sci. 80, 7586–7590.*
Laub et al (1983) J. Virol. 48, 271–280.*
Gluzman et al (1982) Eukaryotic Viral Vectors, Cold Spring Harbor Lab. 187–192.*
Osbourne et al. (1982) Cell 29: 139–48.
Laub et al. (1983) J. Virology 48: 271–80.
Kruczek et al. (1983) PNAS 80: 7586–90.
Gluzman (1982) pp 187–92 in *Eukaryotic Viral Vectors*.
Osborne et al, (1982) Cell 29: 138–48.*
Laub et al. (1983) J.Virology 48: 271–80.*
Kruczek et al. (1983) PNAS 80: 7586–90.*
Gluzman et al. (1982) in Eukaryotic Viral Vectors, Cold Spring Harbor, ed. Gluzman, pp. 187–92.*
Fundamental Virology, Chpater 31, Horiwitz, pp. 771–813, 1991.
Laub et al J. of Virol 48(1): 271, 1983.
Gluzman et al Erkaryotic Viral Vectors, 1982, 187–192.
Michel et al. PNAS 81 7708, 1984.
Ballay et al EMBO J 4(13B): 3861, 1985.*
Michel et al PNAS 81: 7708, 1984.*
Verma et al., Gene therapy–promises, problems and prospects, 1997, Nature, vol. 389, pp. 239–242.*
R. Crystal, Transfer of genes to humans: Early lessons and obstacles to sucess, 1995, Science, vol. 270, pp. 404–410.*
M. Deonarain, Ligand–targetes receptor–mediated vectors for gene therapy, 1998, Exp. Opin. Ther. Patents, vol. 8, No. 1, pp. 53–69.*
Miller et al., Targeted vectors for gene therapy, 1995, FASEB, vol. 9, pp. 190–199.*
Osborne et al., Cell, 29:139–148 (1982).
Laub et al., J. of Virology, 48:271–80 (1983).
Kruczek et al., PNAS, 80:7586–90 (1983).
Gluzman, Eukaryotic Viral Vectors, Cold Springs Harbor Laboratory, ed. Gluzman, pp. 187–92 (1982).
Crowley et al., Mol Cell. Biology, 3:44–55 (1983).
Michel et al., PNAS, 81: 7708–7712 (Dec. 1984).
Sassone–Corsi et al., Nucleic Acids Research, 11:8735–8745 (1983).
Fire et al., Chem. Abs., 96:123, 63555n (1982).
Nevins et al., Chem. Abs., 102:158, 185553s (1985).
Oda et al., Chem. Abs., 98:191, 28934e (1983).
Tiollias et al., Chem. Abs., 100:119, 1352m (Jan. 2, 1984).
Gaynor et al., Chem. Abs., 101:177, 18453p (1984).
Berkner et al., Nucleic Acids Research, 12:1925–1941 (1984).
Graham et al., J. Gen. Virology, 36:59–72 (1977).
Inge Kruczek et al., Proc. Natl. Acad. Sci. USA 80: 7586–7590 (1983).

(List continued on next page.)

*Primary Examiner*—Michael C. Wilson
(74) *Attorney, Agent, or Firm*—Finnegan, Henderson, Farabow, Garrett & Dunner, L.L.P.

(57) ABSTRACT

Recombinant DNA modified by a nucleotide sequence coding for a specific polypeptide sequence whose expression is sought, this recombinant DNA being appropriate to the transformation of eucaryotic cell lines, notably human or animal, the endogenous polymerases of which are susceptible of recognizing the adenovirus promoters. The DNA according to the invention is more particularly characterized by the fact that the said insertion nucleotide sequence is placed under the direct control of the early promoter of the E1A region of the genome of adenovirus.

24 Claims, 4 Drawing Sheets

OTHER PUBLICATIONS

Kathleen Berkner et al., Nucl. Acids Res. 12: 1925–1941 (1984).
Y. Gluzman, Eukaryotic Viral Vector, Cold Spring Harbor Laboratory (New York, 1982) pp. 187–192.
F. L. Graham et al., J. Gen. Virol. 36: 59–72 (1977).
Paolo Sassone–Corsi et al., Nucl. Acids Res. 11: 8735–8745 (1983).
Marie–Louise Michel et al., Proc. Natl. Acad. Sci. USA 81: 7708–7712 (1984).
Orgad Laub et al., J. Virol. 48: 271–280 (1983).
Timothy Osborne et al., Cell 29: 139–148 (1982).
Timothy Osborne et al., J. Virol. 45: 594–599 (1983).
Kathleen Berkner et al., Adenovirus Vectors pp. 193–198.
Craig Crowley et al., Mol. Cell. Biol. 3: 44–55 (1983).
Nevins et al., Chem. Abs., 102:158, 18553s (1985).
Oda et al., Chem. Abs., 98:191, 28934e (1983).
Tiollas et al., Chem., Abs., 100:119, 1352m (1984).
Gaynor et al., Chem. Abs., 101:177, 18453p (1984).
Fire et al Chem. Abstr. 96:123, 63sss, 1982.
Osborne et al. (1982) Cell, 29: 139–48.
Laub et al. (1983), J. Virology, 48: 271–80.
Kruczekl et al. (1983), Proc. Natl. Acad Sci. 80, 7586–90.
Gluzman et al. (1982), Eukaryotic Viral Vectors, Cold Spring Harbor Labs, ed. Gluzman, pp. 187–92.
Berkner et al., Nucleic Acids Research, 12: 1925–41 (1984).
Graham et al., J. Gen. Virology, 36: 59–72 (1977).
Nevins et al., Chem. Abs., 102: 158, 18553s (1985).
Oda et al., Chem. Abs., 98: 191, 28934e (1983).
Tiollas et a., Chem. Abs., 100: 119, 1352m (Jan. 2, 1984).
Gaynor et al., Chem. Abs., 101: 177, 18453p (1984).
Crowley et al., Mol. Cell. Biology, 3: 44–55 (1983).
Michel et al., PNAS, 81: 7708–12 (Dec. 1984).
Sassone–Corsi et al., Nucleic Acids Research, 11: 8735–45 (1983).
Fire et al., Chem. Abs., 96: 123, 63555n (1982).
Graham et al. , 36 J. Gen. Virol., 59–74 (1977).
Anderson, et al., 226 Science 401, 402 (Oct. 26, 1984).

* cited by examiner

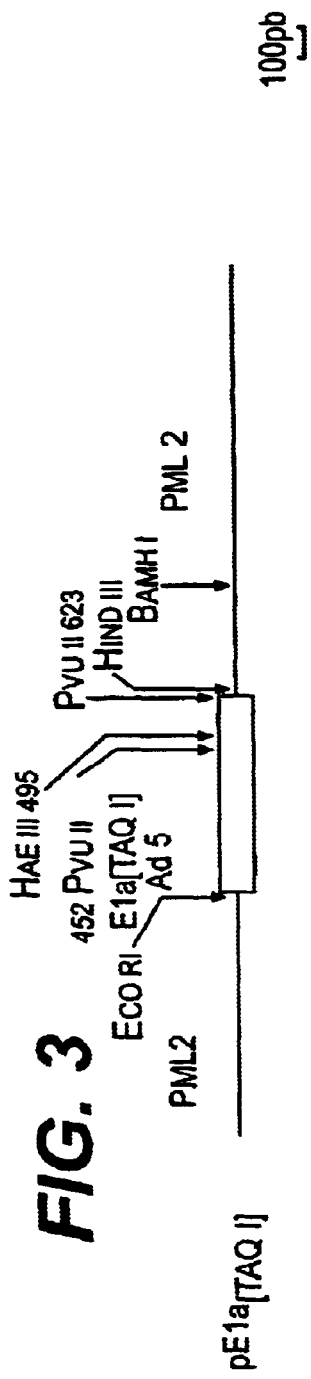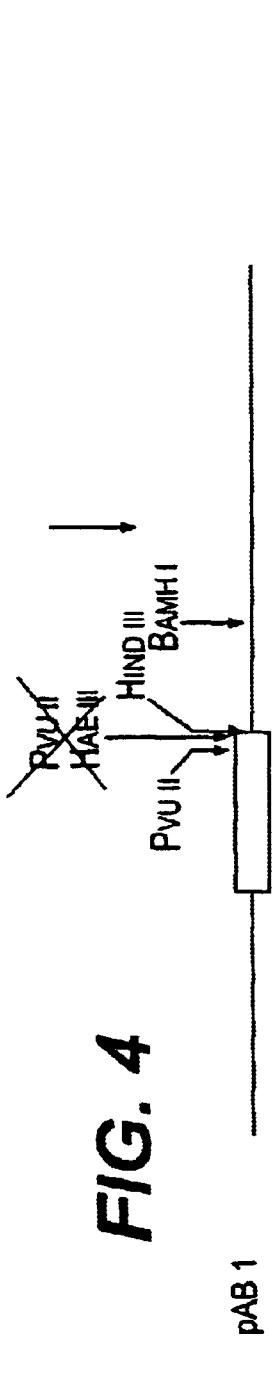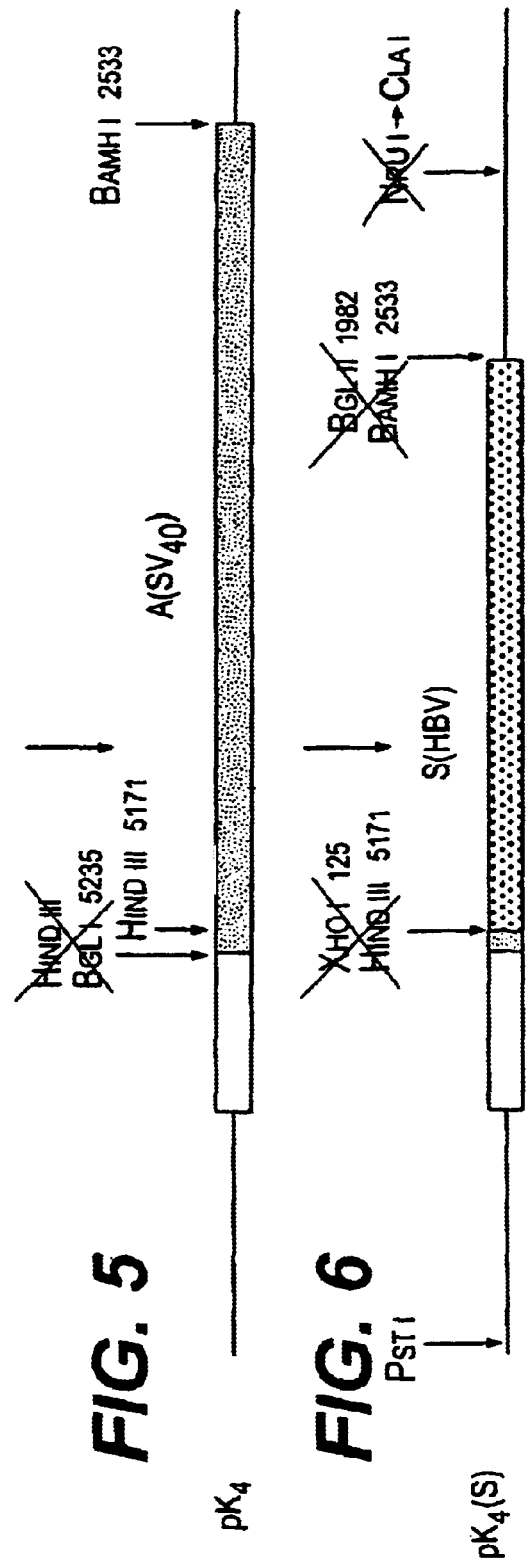

ADENOVIRAL VECTOR WITH A DELETION IN THE E1A CODING REGION EXPRESSING A HETOROLOGOUS PROTEIN

This a continuation of application Ser. No. 07/935,459, filed Aug. 26, 1992, now abandoned, which is a continuation of application Ser. No. 07/790,080, filed Nov. 13, 1991, now abandoned, which is a continuation of application Ser. No. 07/456,200, filed Dec. 20, 1989, now abandoned, which is a continuation of application Ser. No. 07/293,556, filed Jan. 5, 1989, now abandoned, which is a continuation of application Ser. No, 06/799,938, filed Nov. 20, 1985, now abandoned.

The invention concerns a recombinant DNA including a nucleotide sequence coding for a specific polypeptide under the control of an adenovirus promoter, the vectors containing this recombinant DNA, the eucaryotic cells transformed by this recombinant DNA, the excretion products of these transformed cells and their applications, notably to the constitution of vaccines.

Human adenoviruses possess a long (around 36,000 bp) linear and double-stranded genome which codes for at least 30 proteins. The viral cycle, in the course of the infection of permissive cells, is divided into two phases, early and late. It is known that the four regions of the viral genome expressed in the early phase are called regions E1, E2, E3, and E4, whose respective positions in the whole genome are schematically represented in FIG. 1. The E1 region, situated at the left end of the genome, is itself divided into two regions, E1A and E1B. The passage from the early phase to the late phase, marked by the replication of the viral DNA, is characterized by an abrupt change in the genetic program of the virus. The expression of certain early genes is repressed while the transcription of the late genes is accomplished principally via only one promoter, the major late promoter (FIG. 1). In addition, a strong repression of protein synthesis of the host cell may be observed.

The genetic organization of type 2 or 5 human adenovirus (Ad2, Ad5) is sufficiently well known that their genome may be manipulated in vitro and its use as a vector for the expression of a foreign gene in an animal cell in culture has already been envisaged. Indeed it is known that the E3 region, which represents 6% of the genome, is not essential in vitro and may therefore be substituted in its entirety. The size of the foreign DNA fragment which it is possible to insert into the genome of these viruses, is large. In fact, the virus may encapsulate a genome whose length exceeds by 5% that of the wild genome.

Different vectors derived from adenoviruses of type 2 or 5 have therefore been constructed. In these recombinants, the foreign gene was expressed under the control of the major late promoter. This has permitted the obtaining in certain cases of a synthesis of the protein coded by a foreign gene at a level comparable to that of the late viral proteins. This being the case, it results from the preceding that the expression of the foreign gene under the control of the late promoter can only manifest itself in the late phase of the viral cycle.

The invention results from the observation that the promoter of the early region E1A of the genome of an adenovirus (hereafter designated simply as "E1A promoter") could control in a particularly effective manner the expression of a heterologous gene (that is, foreign vis-a-vis the genes normally associated with it in the adenovirus) or more generally of a heterologous nucleotide sequence coding for a polypeptide sequence whose expression is sought. In other words, the E1A promoter acts like a strong promoter, and this more particularly when the E1A promoter combined with the heterologous coding sequence is inserted into a viral vector.

The invention therefore concerns in a general fashion a recombinant DNA for the transformation of eucaryotic cell lines, notably human or animal, chosen from among which are infectable by the adenoviruses or whose endogenous polymerases are likely to recognize the adenovirus promoters, this recombinant DNA being, in addition, modified by an insertion nucleic acid containing a nucleotide sequence coding for a polypeptide sequence whose expression in the said cell lines is sought. This recombinant DNA is more particularly characterized by the fact that the said insertion sequence is placed under the direct control of the early promoter of the E1A region of the genome of the adenovirus.

Preferably, this recombinant DNA is incorporated into a replicatable vector in the said cell lines or associated by genetic recombination with such a vector.

Being a viral vector, notably one derived from adenovirus, equally offers the advantages attached to the E1A region of the adenoviruses, namely that its expression is constitutive and permanent all during the viral cycle.

A particularly prefered form of the recombinant DNA according to the invention is characterized by the fact that it includes, 'downstream' of the insertion nucleic acid, in the direction of transcription, a defective adenovirus genome including nevertheless all of those of the essential sequences necessary to the replication of the corresponding adenovirus, which are normally situated 'downstream' of the genes normally under the direct control of the E1A early promoter in the said genome.

Advantageously, the defective adenovirus genome with which the recombinant DNA conforming to the invention is associated, is constituted of complete adenovirus genome, deprived however of the anterior part of the E1A region of the viral genome, notably of its 0–2.6% fragment (the percentage expressed relative to the total size of the adenovirus genome).

The recombinant DNAs of the invention, associated with the elements of vectors such as those which have been mentioned above, constitute in fact the vectors will again be the case where reference is made to "defective recombinant viruses", when the elements of the vectors associated with the recombinant DNA of the invention will be derived from a defective genome of adenovirus. These defective recombinant viruses are advantageously used for the transformation of transformable cell lines from superior eucaryotes (notably of human or animal origin) themselves including a distinct sequence of nucleotides apt to complement the part of the genome of the adenovirus which is missing from the aforesaid vector, the said distinct sequence preferably being incorporated into the genome of the cells of the said cell line.

As a prefered example of such cell lines, one might mention the line 293, a human embryonic kidney line which contains, integrated into its genome, the first eleven percent of the left end of the genome of an Ad5. This permits the complementing of the defective recombinant viruses which have deletions of this region.

The use of these systems: defective recombinant virus vector—cells containing a sequence capable of complementing the defective recombinant viruses, is of a very particular interest, when the nucleotide sequence contained in the insertion nucleic acid of the recombinant DNA codes for a protein which, when it is expressed in the natural cellular host under the control of its natural promoter, is excreted into the culture medium of this natural cellular host.

The S gene of the genome of the virus of hepatitis B constitutes in this regard a nucleotide sequence of particular interest, arid this for several reasons. On the one hand, the product of the expression of the S gene in the cells which express it, HBsAg, is secreted into the cellular supernatant in the form of particles which are easy to detect and to quantify by radio-immunology, which permits a precise evaluation of the capacity of expression of the viral vector. On the other hand, the invention provides a recombinant viral vector permitting the study of the expression of the genes of the HBV at the level of transcription as well as that of translation, which is all the more interesting in that until now there had not existed a cell culture system capable of propagating the hepatitis B virus (HBV). And lastly, the cellular infection by the adenovirus-HBV recombinant virus illustrates particularly well the methodological basis of a process for the manufacture of a vaccine against a given pathologic agent (in this case the hepatitis B virus in the example under consideration). Another nucleotide sequence of the genome of the hepatitis B virus of particular interest is the S gene along with its pre-S2 region which codes for the HBs antigen and for a receptor of polymerized human serum albumen (pHSA) (25, 26).

It goes without saying that one may substitute for the S gene into the recombinant DNA, any other nucleotide sequence coding for a distinct antigen-protector against another given pathogenic agent, especially when this distinct antigen-protector is itself normally susceptible of being secreted by the cells transformed by the recombinant DNA. It equally goes without saying that in the recombinant DNA the S gene and the pre-S2 region may be replaced any other nucleotide sequence coding for a distinct antigen-protector against another given pathogenic agent, especially when this distinct antigen-protector is itself normally susceptible of being secreted by the cells transformed by the recombinant DNA. The nucleotide sequence coding for this distinct antigen-protector may possibly be inserted into the recombinant DNA in phase with another genes for example the HBsAg antigen, if and when that other gene may be used as the "locomotive" for the promotion of the excretion equally of this distinct antigen, notably in the form of a hybrid protein. As an example of the distinct antigens susceptible of being thus produced (if need be, in the hybrid protein form), the structural glyco-proteins of the Epsteim-Barr virus may be mentioned.

The first nucleotides of the nucleotide sequence coding for a specific polypeptide (a "simple" or hybrid protein) are placed, notably by construction, as close as possible to this promoter, notably to the "TATA box", which is characteristic of the promoter, it being understood however that the nucleotide sequence between the promoter and the ATG initiator of the nucleotide sequence coding for the said specific polypeptide should in general contain the triplets coding for the non-translated 5' end of the messenger RNA corresponding normally to the coding sequence and containing the matching sequences to the ribosomes necessary to an effective translation. This untranslated 5' end of the messenger RNA could also be replaced by the untranslated 5' end of a messenger RNA distinct from that normally associated with a specific coding sequence. For example, one may, in the case of the S gene, replace the untranslated 5' end containing the pre-S gene or juxtaposing this with the untranslated 5' end of the messenger RNA of the T antigen of SV40. But it has also been noted that when using a DNA sequence containing the o and pre-S2 regions of the genome of the hepatitis B virus under the control of the strong promoter, E1A, it is possible to obtain the expressions both of the pre-S2 and the S regions. Any other untranslated 5' end of messenger RNA may be used if it is compatible Smith the other similar chosen end.

It is advantageous that the distance between the TATA box of the promoter and the initiation site of the messenger RNA should be around 30 nucleotides.

The E1A promoter of the recombinant DNA according to the invention and more generally the vector according to the invention using the more important parts of the adenovirus genome are preferably derived from an adenovirus belonging to category C, as defined by TOOZE. These adenoviruses have the known property of not being oncogenic. The sub-types Ad2 or Ad5 of this category of adenovirus are characterized by an important transforming power. The use of this latter type of recombinant DNA is therefore particularly recommended, when the desired expression product is intended for the production of antigen-protectors, notably the active principles of vaccines. This will be even more true in the case where whole adenoviruses, and even infectious, will be used as the active principles of live vaccines, notably under the conditions which will be spelled out further on.

The invention naturally equally concerns the cell lines, notably of human or animal origin, which are transformed by the recombinant DNAs as defined hereabove and which are rendered capable of synthesizing a polypeptide coded by the nucleotide sequence (or the said nucleotide sequences) contained in these recombinant DNAs and placed under the direct control of said promoter.

The invention concerns more particularly yet the cell lines transformed with the recombinant DNA conforming to the invention and in addition characterized in that the cells of the cell lines themselves contain a distinct sequence of nucleotides capable of complementing the part of the adenovirus genome which is missing from the aforesaid vector, the said distinct sequence being preferably incorporated into the genome of the cells of the said cell line.

In this regards the line 293 already mentioned above, after having been transformed by the recombinant DNAs, constitutes a prefered cellular culture according to the invention. Due to the complementation sequence contained by the cells of this line, a major viral multiplication within these cells is observed and, by way of consequence, an equally multiplied expression of the sequence coding for the predetermined polypeptide. In the first case where this coding sequence is the S gene, a high production is obtained of the HBsAg antigens excreted into the culture medium of these cells. In the second case where the coding sequences are constituted of the S gene and the pre-S2 region of the hepatitis B virus, the recombinant adenovirus directs in vitro the synthesis of the HBsAg particles possessing an activity for the pHSA receptor. Injected into rabbits this recombinant virus produces anti-HBsAg and anti-pHSA antibodies. This shows the possibility of using the recombinant adenovirus to express a gene both in vitro and in vivo. The same vectors may be used for the transformation of Vero cells under analogous conditions.

The vectors containing the recombinant DNA according to the invention may equally be used for the transformation of cells not possessing themselves the complementation sequence under the conditions which have been indicated hereabove. It may then be necessary to proceed to a co-transformation of these latter types of cells, on the one hand, with a vector containing the recombinant DNA according to the invention, and on the other, with a non-defective adenovirus or a distinct recombinant DNA containing the adenovirus sequences which are missing from the recombinant vector conforming to the invention. It may certainly be observed in this latter case a simultaneous production of HBsAg antigens (when the coding sequence contains the S gene) arid of the adenovirus replicated and liberated by the cells thus transformed. The antigen-protector formed may however be separated from the viral suspension, if need be, for example by bringing the culture medium into contact with anti-adenovirus antibodies, preferably immobilized on a solid support, such as reticulated agarose, sold under the designation, SEPHAROSE. In any case, the presence of residual quantities of the virus in the vaccinating preparation is only of a relatively minor importance. Indeed, the adenovirus has only a weak pathogenicity in humans, causing no more than benign respiratory infections.

The small importance of the pathogenicity of the adenoviruses, more particularly of those belonging to group C of the human adenoviruses, allows the contemplation of "living vaccines". These could be constituted of infectious adenoviruses modified at the level of the E3 region by the insertion of the recombinant DNA according to the invention in the non-essential part of the adenovirus. In this regard, the fact must be emphasized that the human adenoviruses of the C group have never proved to be tumorigenic in animals (3). These vectors or viruses will be of a very particular interest for the transformation of Vero cells, the non-tumorigenic character of which has been firmly established. For this reason they constitute a line of animal origin particularly favorable to the production of products for human use.

The supplementary characteristics of the invention will appear yet in the course of the description which follows of the prefered constructions of the vectors containing the recombinant DNA according to the invention and of the conditions under which these vectors are useable. For this, reference will be made to the drawings, in which:

FIG. 1 schematically represents the relative positions of the different regions of the genome of an adenovirus of sub-type Ad5, and, at a larger scale, of the E1A region of this genome;

FIGS. 3 to 6 show the successive constructions leading to the realization of a plasmid containing a first recombinant DNA conforming to the invention (FIG. 6); and FIG. 3 schematically represents the construction of the pE1a plasmid and relevant restriction sites.

FIG. 4 schematically represents the construction of the pAB1 plasmid and relevant restriction sites.

FIG. 5 schematically represents the construction of the pK4 plasmid and relevant restriction sites.

FIG. 6 schematically represents the construction of the pK4(S) plasmid and relevant restriction sites.

Figure 7:
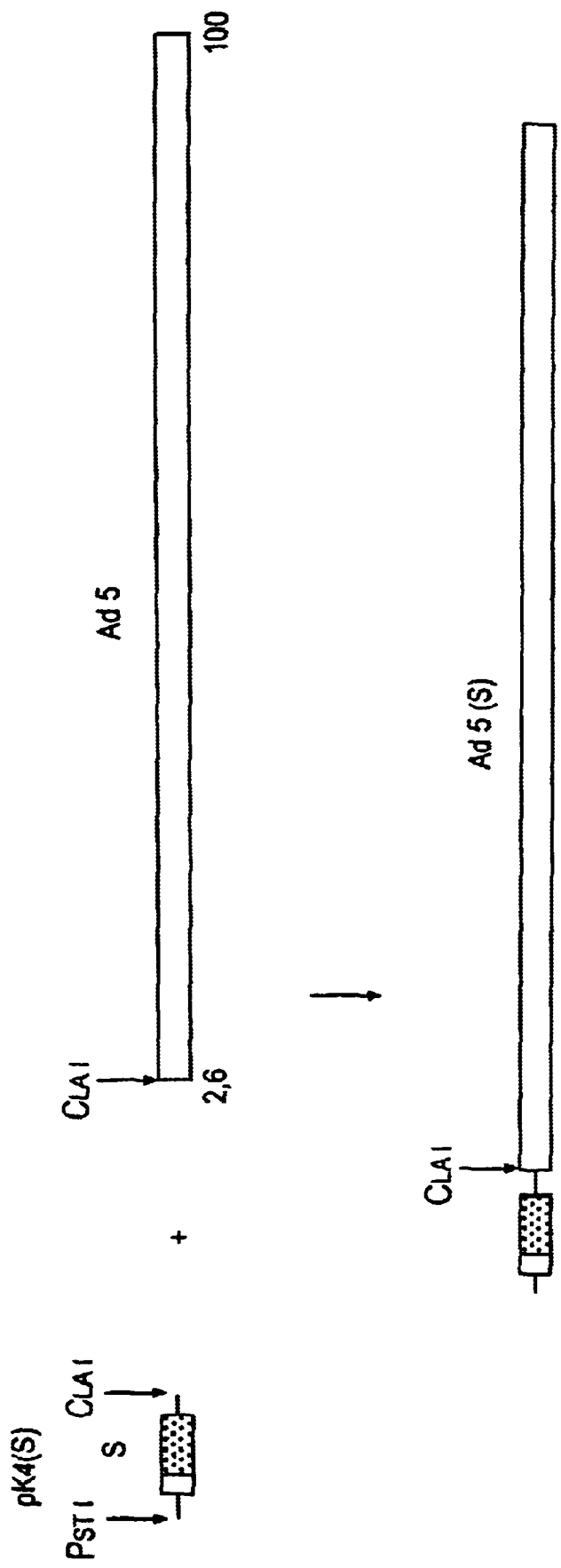

FIG. 7 schematically represents the construction of a "defective recombinant virus" starting from the modified plasmid of FIG. 5 and the defective genomes of Ad5.

First, the following observations will be made concerning the figures, before describing the realization of the construct ion of the recombinant DNAs according to the invention.

In FIGS. 3 to 6, the parts drawn with a fine line correspond to sequences of the plasmid pML2.

The numbers appearing in the FIGS. 1 to 5 indicate the positions of the restriction sites in the viral sequences: Ad5, SV40, and HBV. The numbering of the positions of the restriction sites for Ad5 and SV40 is that of J. TOOZE and for HBV is that of P. TIOLLAIS et al.

The site designations which have been crossed out in the drawings bear witness to the former presence of these same sites in the corresponding parts of the DNAs which will be described hereafter. These sites have meanwhile been deleted, suppressed by repairing the cohesive ends of the fragments opened or fragmented with the aid of the corresponding restriction enzymes, or by any other means such as envisaged in the description which follows of the constructions which have been made.

1. Reminder of the Principle Elements of the Structure and of the Organization of the Genome of the Adenovirus Ad5 (Hereafter Often Simply Designated as Ad5)

Figure 1:
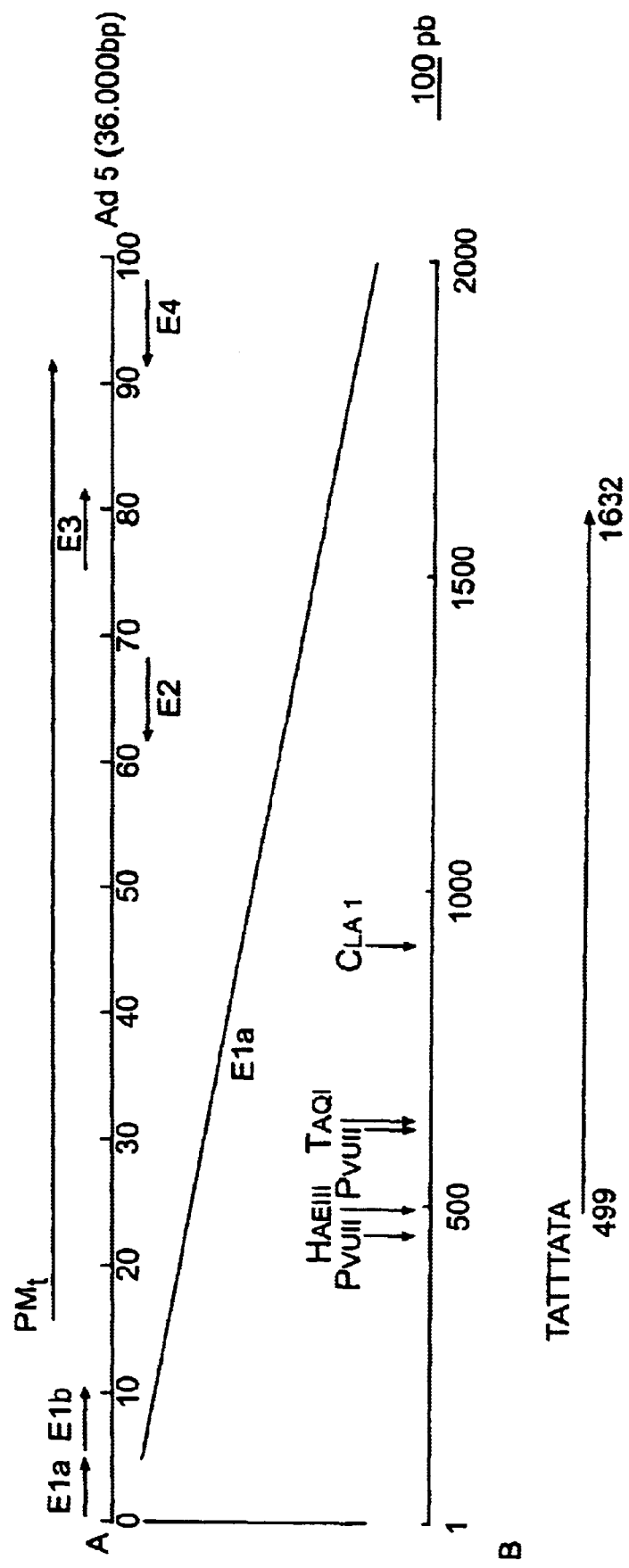

They result in the parts 1A and 1B of FIG. 1.

1A: The genome is linear, double-stranded molecule of DNA of around 36,000 bp. The arrows indicate the position and the direction of the transcriptions of the early regions E1A, E1B, E2, E3, and E4. The major late promoter, $PM_t$ ("promoteur majeur tardif"), and the transcription unit associated with it are equally shown. The numbering, by tens, from 0 to 100, corresponds to the sizes expressed as a % of the length of the total genome.

1B: The region E1A. The transcripts of this region all have identical 5'P (position 499) and 3'OH (position 1632) ends. The first T of the TATE element of the promoter is situated at position 468. The restriction sites used in the plasmid constructions are indicated. The sizes are expressed by the number of base pairs.

2. Origin of the Fragments Containing the S Gene or the S Gene and the pre-S2 Region Utilized in the Constructions which Follow First case: The fragment of the genome of the hepatitis B virus containing the S gene.

Figure 2:
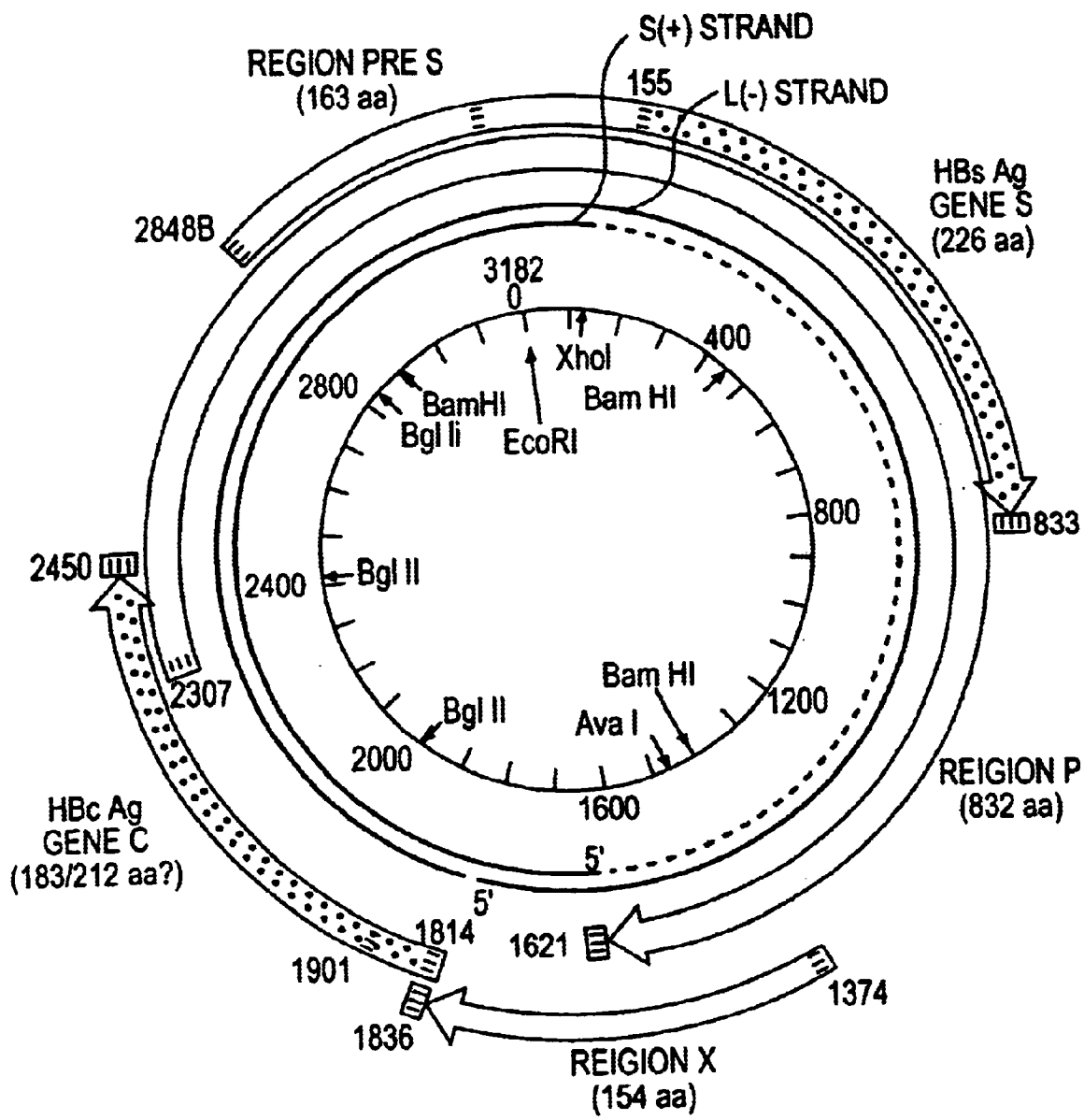
FIG. 2 is a now classic diagram of the genome of the virus of hepatitis B.

It is derived from the genome of the virus of hepatitis B (FIG. 2). It is to be recalled that the genome of the hepatitis B virus is a circular molecule of DNA partially single-stranded. Its length is around 3,200 dp. It is constituted by the pairing of two strands of unequal length called strands L(−) and S(+). The S gene represents the coding sequence of the major polypeptide of the viral envelope of the HBsAg. The DNA fragment used in the constructions below is the $XhoI_{127}$-$BglII_{1984}$ fragment. The polyadenylation site of the HBsAg has been localized at position 1916.

Second case: The fragment of the genome of the hepatitis B virus containing the S gene and the pre-S2 region.

The DNA fragment utilized is the $MstII_{3161}$-$BglII_{1982}$ which codes both for the HBs antigen and for a receptor of polymerized human serum albumin (pHSA). The MstII site precedes the initiation codon of the pre-S2 region of 9 nucleotides. The BglII is situated 64 nucleotides further on from the poly A addition signal of the S gene.

It is a question in what follows of the construction and of the propagation of a recombinant adenovirus which includes the S gene. The operating method is identical to obtain a recombinant adenovirus, conforming to the invention, possessing the S gene and the pre-S2 region, it being understood that, in the second case, it is the MstII-BglII fragment of DNA which is inserted between the HindIII and BamHI restriction sites of the plasmid pK4, in place of the XhoI-BqlII DNA fragment discussed below.

In what follows, the recombinant adenovirus possessing the S gene will be designated as Ad5(X-B) and the recombinant adenovirus possessing the S gene and the pre-S2 region as Ad5(M-B).

3. Construction of the Plasmid pE1A (TaqI) (FIG. 3)

The plasmid pE1A(TaqI) contains the first 632 nucleotides of the left end of the Ad5 genome. This fragment has been obtained by cutting of the purified SacI E restriction fragment (0–5.0%) of Ad5 by TaqI. (FIG. 1). This fragment has been inserted between the EcoRI and ClaI restriction sites of the pML2 plasmid (FIG. 3). The pML2 plasmid has been opened by EcoRI and ClaI. The Ad5 fragment has been bound to the linearized plasmid at the level of the TaqI end. The junction of the TaqI-ClaI ends re-creates a ClaI restriction site. The EcoRI end of the recombinant has been repaired with the DNA-polymerase I of *E. coli* (Klenow's fragment) and the plasmid re-circularized by means of the ligase T4. The EcoRI site has therefore been reconstituted.

4. Fabrication of the Plasmid pAB1 (FIG. 4)

The pAB1 plasmid has been constructed from the pEIA (TagI) plasmid, in a way so as to eliminate the coding part of the E1A region. This has been carried out by isolation of the PvuII-PvuII fragment (positions 452–623), cutting of this fragment by the enyme HaeIII (position 495), and reinsertion of the $Pvu_{452}$-$Hae_{495}$ fragment at the level of the $PvuII_{623}$ site of the pE1A(TaqI) plasmid. In other words, the $HaeIII_{495}$-$PvuII_{623}$ fragment has been deleted. The pAB1 plasmid contains a HindIII site close to the transcription initiation site of the E1A region and a BamHI site (of pML2) situated at a distance. These two restriction sites may be used to clone foreign genes without genetic fusion.

5. Production of the Plasmid pK4 (FIG. 5)

pAB1 has been cut by HindIII and BamHI and the fragment containing the E1A promoter, issued from pAB1, has been linked, at the level of its BamHI end to the BqlI-BamHI fragment (positions 5235–2533 of the genome of the SV40 virus) hereafter called A(SV40) containing the gene coding, for the T and t antigens of the SV40 virus. After repairing of the BglI and HindIII ends of the reconstituant by Klenow's fragment, the plasmid is re-circularized by means of the liqase T4. The present construction in the pK4 plasmid has been tested by bringing into play the transitory expression of the T gene. Introduced into HeLa cells by transfection according to the calcium phosphate technique the pK4 plasmid directs the synthesis of the T antigen of SV40 which has been detected by immunofluorescence. Around 1% of the transfected cells presented a clear fluorescence. The absence of fluorescence after cellular transfection by a plasmid containing the fragment of SV40 inserted in the wrong orientation shows that the gene of the T and t antigens is well placed under the control of the E1A promoter of the Ad5.

It is the HindIII site, at position 5171 of the A(SV40) fragment which is then used to substitute the aforesaid fragment containing the S gene for the major part of A(SV40).

6. Production of the Plasmid pK4S(X-B) (FIG. 6)

The pK4 plasmid has been digested by HindIII and BamHI. The XhoI-BglII fragment (positions 125 to 1982) of the genome of the hepatitis B virus (HBV) (FIG. 2) has been inserted, instead and in the place of the major part of A(SV40) between the HindIII and BamHI restriction sites of the pK4 plasmid, after repairing of their respective ends by the DNA polymerase I of *E. coli* (Klenow's fragment) (FIG. 3). The XhoI, HindIII, BamHI and BglII restriction sites are lost after ligation.

The HindIII site was situated at 8 nucleotides before the ATG initiator of the T and t antigens. The insertion of the S gene into this site therefore permits the conservation of the 5' end of the early mRNA of SV40 containing the "capping" site and the pairing sequences of the messenger to the ribosomes. The HBV DNA fragment contains the coding sequence or S gene (position 155 to 833) of the major polypeptide of the viral envelope bearer of the HBsAg as well as the sequence situated in 3' of the S gene and which includes the polyadenylation site off the messenger RNA of the HBsAg at position 1916. Two plasmids, $pK4S^+$ and $pK4S^-$, bearers of the HBV fragment inserted in both directions have been isolated. 293 cells have been transfected by these two plasmids and the synthesis of HbsAg was sought in the cellular supernatant 3 days after the transfection. Only the $pK4S^+$ plasmid which possesses the E1A promoter at the 5' end of the S gene is capable of directing the synthesis of HbsAg. This shows that the expression of the S gene is indeed under the control of the E1A promoter of Ad5. Finally, a non-methylated ClaI restriction site in *E. coli* has been introduced into the plasmid $pK4S^+$ (X-B) at the level of the NruI site of the $pML_2$ sequence. The site is necessary to the construction of the recombinant virus.

It is finally the fragment delimited by the PstI and ClaI ends, and obtained from pK4S(X-7B), which has been used for the fabrication of a "defective recombinant virus" conforming to the invention.

7. Construction of the Defective Recombinant Virus (FIG. 7)

3 micrograms of the PstI-ClaI restriction fragment purified from the $pK4S^+$ (X-B) plasmid have been ligated to 20 micrograms of the ClaI restriction fragment (2.6%–100%) of the Ad5 purified by ultracentrifugation in a sucrose gradient to provide the "defective recombinant virus" Ad5.

8. Propagation of the Recombinant Virus

The 293 cells have been cultured in dishes 6 cm in diameter. 4 hours before transfection the supernatant of the culture has been replaced by medium. 5 dishes of 293 cells at 70% confluence were then trarisfected with the ligation mixture according to the calcium phosphate technique then incubated for 4 hours at 37 degrees C. After adsorption, the cells contained in each dish have been washed with 2 ml of TS buffer (NaCl 8000.0 mg/l, KCl 380.0 mg/l, $Na_2HPO_4$ 100.0 mg/l, $CaCl_2$ 100.0 mg/l, $MgCl_2,6H_2O$ 100.0 mg/l, Tris 3000.0 mg/l, pH 7.4), treated with 400 microliters of a TS solution containing 20% glycerol for 1 minute at ambient temperature, washed twice with 2 ml of TS buffer, then re-covered with 4 ml of MEM medium containing 1% noble agar, and 1% fetal calf serum. At days 4 and 7, the cells have been re-covered with 4 ml of nutrient mix. At day 10, the cells have been stained with 4 ml of nutrient medium supplemented with 0.01% neutral red. The plagues have been observed on day 11. The virus have been resuspended in 1 ml of TS and amplified on 293 cells. The presence of HBsAg in the culture medium has been tested by RIA ("radio-immunoassay")(Austria II, ABBOTT Laboratories). After amplification, the presence of HBV sequences in the recombinant has been tested by hybridization. Five plagues have been analyzed. Only one contained a recombinant $HBsAg^+$ virus. This Ad5(X-B) clone along with another clone were positive for the detection of the HBV sequences. The size of the recombinant viral genome exceeds that of the wild virus of 2100 bp. No deletions could be detected by analysis of the restriction fragments of the genome. In addition, this analysis has shown that the PML2 sequences situated between the PstI restriction site and the Ad5 sequence have been correctly excised during the propagation of the recombinant nenome in the 293 line.

9. The Synthesis of HBsAg Directed by the Ad5 (X-B)

The 293 cells and Vero cells have been infected with Ad5(X-B) virus. The levels of expression of HBsAg synthesized are shown in Table I. Samples of the cellular supernatant have been taken 3 days after infection and the HBsAg sought by RIA. The results show that the Ad5(X-B) vector is capable of directing the synthesis of HBsAg in the two cell lines, and the excretion of HBsAg by the cell lines into their respective culture mediums.

The synthesized HBsAg has been purified by ultracentrifugation in CsCl. It has a density of 1.20. The typical particles of 22 nm have been observed under electron microscopy.

10. Synthesis of HBsAg Directed by Ad5(M-B) Vectors

The levels of expression of HBsAg synthesis after infection of 293 and Vero cells by Ad5(M-B) are shown in Table I.

The extra- and intra-cellular distribution kinetics of HbsAg starting from Vero cells infected by Ad5(M-B) have indicated that the synthesis of HBsAg commenced 3 hours after infection and could be detected in the medium after 8 hours. The infection by the recombinant virus Ad5(M-B) has led to an accumulation of HBsAg of 4.5 to 1 microgram/$10^6$ cells in the medium after 120 hours. Repeated exeriments have shown that the recombinant virus containing the pre-S2 region synthesizes greater quantities of HBsAg than the recombinant virus containing only the S gene. The HBsAg purified from the culturemedium of cells infected with the recombinant adenovirus Ad5(M-B) consisted of a homogenous population of particles having a mean diameter of 22 nm. The density after centrifugation in CsCl was 1.21.

11. Activity of the pHSA Receptor of the HBsAg Particles Issued from Vero Cells The HBsAg particles produced in the Vero cells have been tested by the technique of hemagglutination of sheep red blood cells coated with pHSA and by RIA to detect an activity of the receptor for the pHSA. A binding activity for pHSA has been detected, but not for polymerized bovine albumin (Table II). No such activity could be detected with Vero cells infected by the recombinant adenovirus Ad5(X-B) containing only the S gene.

12. In Vivo Activity of the Recombinant Virus

Rabbits have been intravenously inoculated with highly purified preparations of Ad5(M-B) recombinant adenovirus and of wild adenovirus. Although the HBsAg antigen could not be detected in their serum, 5 rabbits out of 8, inoculated with the recombinant virus, showed the appearance of an anti-HBs titer varying from 20 to 270 mIU/ml after 15 days (Table III). No anti-HBs antibodies were detected in the rabbits injected with the wild type adenovirus. After a second intravenous inoculation 4 weeks after the first, a second peak attaining 440 mIU/ml for one of the animals was observed in the anti-HBs response. 4 weeks after the second injection, the anti-HBs titers varied from 6 to 360 mIU/ml. Prior studies have indicated that the minimum anti-HBs level still offering protection against HBV in humans is 10 mIU/ml. Anti-pHSA antibodies were sought in the inoculated rabbits in order to determine their relationship to the neutralization of the HBV. These antibodies, detected by the inhibition of hemagglutination, have been found in 5 animals out of 5 having a positive anti-HBs response (Table IV).

The recombinant adenovirus Ad5(M-B) therefore directs in vivo the synthesis of HBsAg particles having the character of a receptor for polymerized human serum albumin.

The invention therefore furnishes a methodological basis for the fabrication of a vaccine against hepatitis B (or against other types of disease) in cell cultures.

The value of using adenoviruses of type 5 as a vector is two-fold. On the one hand, the pathogenicity of this virus in humans is very low, causing only mild respiratory infections. On the other, this serotype which belongs to group C of the human adenoviruses is not tumorigenic in animals. In addition, the rate of HBsAg production obtained on Vero cells (around 1 microgram/$10^6$/infectious cycle) is, a priori, the most favorable to the production of a product for human use.

As it goes without saying and as it results anyway from the preceding, the invention is in no way limited to the modes of application and of realization which have been especially outlined here; but on the contrary it embraces all variants; among these variants, it is appropriate to mention the other forms of vectors containing the recombinant DNA according to the invention, notably the plasmids. These may be, either used to create viral vectors of the kind which have been described, or may themselves be used as vehicles for the incorporation of the recombinant DNA into the genome of the cells of superior eucaryotes, notably cell cultures of humans or primates.

Equally it goes without saying that for the 293 cells mentioned above, may be substituted any other higher eucaryotic cells infectable by adenoviruses or susceptible of recognizing the E1A promoter of the adenoviruses, these cells having been modified, by prior incorporation into their own genomes, of a sequence containing the missing parts of the defective recombinant virus according to the invention of the genome of an adenovirus, notably under the control of a strong promoter recognized by these cells, for example of a promoter of thymidine kinase or of a promoter of the SV40 virus. The sequence originating from the adenovirus, then integrated into the genome of the higher eucaryotic cells, may therefore complement the defective viruses conforming to the invention, under conditions analogue to those permitted for the 293 cells. These methods are applicable with particular advantage to Vero cells.

The adenovirus used has been filed the 3rd of August 1984 under the No. I-322 with the C.N.C.M. ("Collection Nationale de Cultures de Micro-organismes") of the INSTITUT PASTEUR of Paris.

The line 293 has been filed with C.N.C.M. the 3rd of August 1984 under the No. I-323.

TABLE I

| | Time course of extracellular HBsAg production | | | |
|---|---|---|---|---|
| Day | Ad5(X-B) infected Vero | Ad5(X-B) infected 293 | Ad5(M-B) infected Vero | Ad5(M-B) infected 293 |
| 1 | 13 | 15 | 106 | 35 |
| 2 | 17 | 90 | N.D. | N.D. |
| 3 | 45 | 110 | 349 | 56 |
| 4 | 110 | 100 | 668 | 60 |
| 5 | 320 | 130 | 1057 | 63 |
| 6 | 470 | 120 | 1153 | N.D. |
| 7 | 550 | 120 | 900 | N.D. |

The cumulative amounts of HBsAg (ng) produced after infection of 293 and Vero cells by either Ad5(X-B) or Ad5(M-B) are indicated.

TABLE II pHSA receptor activity of HBsAg particles from Vero cells.

| | Cell culture supernatant | | | | | | Human serum | | | |
| --- | --- | --- | --- | --- | --- | --- | --- | --- | --- | --- |
| | Ad5(X-B) | | Ad5(M-B) | | Mock | | HBsAg+ HBeAg+ | | healthy control | |
| | RIA | HA | RIA | HA | RIA | HA | RIA | HA | RIA | HA |
| pHSA | 143 | — | 7512 | 64 | 119 | — | 10472 | 128 | 65 | — |
| pBSA | 58 | ND | 85 | ND | 77 | ND | 145 | ND | 81 | ND |

Results are expressed in cpm for solid phase RIA and in hemagglutination titer (HA).
ND, not determined.
pHSA: polymerized human serumalbumin.
pBSA: polymerized bovine serumalbumin.

TABLE III

Anti-HBs response (mIU ml[1]) in inoculated rabbits.

| | Rabbits | | | | | | | | | |
| --- | --- | --- | --- | --- | --- | --- | --- | --- | --- | --- |
| Weeks | 1 | 2 | 3 | 4 | 5 | 6 | 7 | 8 | 9 | 10 |
| 0 | 0 | 0 | 0 | 0 | 0 | 0 | 0 | 0 | 0 | 0 |
| 1 | 0 | 0 | 2 | 0 | 0 | 30 | 8 | 6 | 12 | 20 |
| 2 | 2 | 0 | 2 | 0 | 2 | 15 | 20 | 270 | 70 | 85 |
| 3 | 0 | 2 | 0 | 0 | 5 | 18 | 13 | 48 | 15 | 11 |
| 4 | 1 | 0 | 0 | 0 | 2 | 21 | 15 | 27 | 17 | 7 |
| 5 | 0 | 0 | 2 | 0 | 2 | 99 | 52 | 440 | 146 | 136 |
| 6 | 0 | 0 | 0 | 0 | 0 | 78 | 26 | 401 | 151 | 148 |
| 7 | 0 | 0 | 0 | 0 | 0 | 20 | 27 | 325 | 58 | 42 |
| 8 | 0 | 0 | 0 | 0 | 0 | 20 | 40 | 367 | 35 | 6 |

** (PFU = plaque forming unit).

Rabbits were injected intravenously with $10^9$ pfu of purified wild-type Ad5 (rabbits 1 and 2) or with $10^9$ pfu of purified adenovirus recombinant Ad5 (M-B) (rabbits 3–10) immediately after the blood drawing in week 0 and week 4. Anti-HBs antibodies have been quantitated using the commercially available RIA Kit AUSAB from Abbott and expressed as International Units (3,5 RIA units are equivalent to 1 mIU).

TABLE IV

Anti-pHSA receptor immune response (reciprocal of the titer)

| | Rabbits | | | | |
| --- | --- | --- | --- | --- | --- |
| Weeks | 6 | 7 | 8 | 9 | 10 |
| 0 | 0 | 0 | 0 | 0 | 0 |
| 1 | 16 | 2 | 2 | 2 | 2 |
| 2 | 4 | 16 | 16 | 16 | 16 |
| 3 | 4 | 4 | 16 | 8 | 8 |
| 4 | 2 | 2 | 4 | 4 | 4 |
| 5 | 16 | 32 | 32 | 32 | 32 |
| 6 | 16 | 32 | 32 | 16 | 32 |
| 7 | 8 | 8 | 32 | 8 | 16 |
| 8 | 4 | 4 | 8 | 4 | 8 |

Rabbits were infected intravenously with $10^9$ pfu of purified adenovirus recombinant Ad5(M-B) in week 0 and week 4. Single animals are identified by the same numbers used in Table 3.

Anti-pHSA receptor activity was expressed as the reciprocal of the highest titer of serum able to give 100% inhibition of hemagglutination. HBsAg particles having a pHSA receptor hemagglutination titer of 1:128 were mixed with an equal volume of serial dilutions of inhibitor sera.

What is claimed is:

1. A method of transferring a nucleic acid sequence encoding a hepatitis B virus S antigen to a mammal to induce an antibody response against HBV S antigen in said mammal, comprising:

administering a defective recombinant Ad2 adenoviral vector to the mammal intravenously, wherein the vector comprises:
    a) an E1A promoter;
    b) a deletion of the entire E1A coding region; and
    c) a nucleic acid sequence encoding the hepatitis B virus S antigen operatively linked to the E1A promoter;

wherein the hepatitis B virus S antigen is expressed in the mammal, thereby inducing an antibody response to the hepatitis B virus S antigen in the mammal, wherein the antibody response is detectable in the blood of the mammal.

2. The method of claim 1, where the mammal is a human.

3. The method of claim 2, wherein the defective recombinant Ad2 adenovirus is administered by intravenous injection.

4. The method of claim 1, wherein the nucleic acid sequence is positioned in the location of the deletion of the E1A coding region.

5. The method of claim 4, wherein the vector further comprises an E3 coding region having a deletion.

6. The method of claim 4, wherein the nucleic acid sequence comprises the S gene of hepatitis B virus.

7. The method of claim 6, wherein the nucleic acid sequence further comprises a pre-S2 gene of hepatitis B virus, wherein the pre-S2 gene is located immediately upstream of the S gene.

8. The method of claim 2, wherein the vector further comprises an E3 coding region having a deletion.

9. The method of claim 8, wherein the nucleic acid sequence is positioned in the location of the deletion within the E3 region.

10. The method of claim 9, wherein the nucleic acid sequence comprises the S gene of hepatitis B virus.

11. The method of claim 10, wherein the nucleic acid sequence further comprises a pre-S2 gene of hepatitis B virus, wherein the pre-S2 gene is located immediately upstream of the S gene.

12. A method of transferring a nucleic acid sequence encoding a hepatitis B virus S antigen to a mammal to induce an antibody response in said mammal comprising: administering a defective recombinant Ad5 adenoviral vector to the mammal intravenously, wherein the vector comprises:

a) an E1A promoter;

b) a deletion of the entire E1A coding region; and c) a nucleic acid sequence encoding a hepatitis B virus S antigen operatively linked to the E1A promoter;

wherein the hepatitis B virus S antigen is expressed in the mammal, thereby inducing an antibody response to the hepatitis B virus S antigen in the mammal, wherein the antibody response is detectable in the blood of the mammal.

13. The method of claim 12, where the mammal is a human.

14. The method of claim 13, wherein the nucleic acid sequence is positioned in the location of the deletion of the E1A coding region.

15. The method of claim 14, wherein the vector comprises an E3 coding region having a deletion.

16. The method of claim 14, wherein the nucleic acid sequence comprises the S gene of hepatitis B virus.

17. The method of claim 16, wherein the nucleic acid sequence further comprises a pre-S2 gene of hepatitis B virus, wherein the pre-S2 gene is located immediately upstream of the S gene.

18. The method of claim 13, wherein the vector further comprises an E3 coding region having a deletion.

19. The method of claim 18, wherein the nucleic acid sequence is positioned in the location of the deletion within the E3 region.

20. The method of claim 18, wherein the nucleic acid sequence comprises the S gene of hepatitis B virus.

21. The method of claim 20, wherein the nucleic acid sequence further comprises a pre-S2 gene of hepatitis B virus, wherein the pre-S2 gene is located immediately upstream of the S gene.

22. The method of claim 6, wherein the antibody response comprises a serum anti-HBs antibody titer of at least 10 mIU/ml.

23. The method of claim 10, wherein the antibody response comprises a serum anti-HBs antibody titer of at least 10 mIU/ml.

24. The method of claim 16, wherein the antibody response comprises a serum anti-HBs antibody titer of at least 10 mIU/ml.

\* \* \* \* \*

UNITED STATES PATENT AND TRADEMARK OFFICE
CERTIFICATE OF CORRECTION

PATENT NO. : 6,696,420 B1
DATED : February 24, 2004
INVENTOR(S) : Michel Perricaudet et al.

It is certified that error appears in the above-identified patent and that said Letters Patent is hereby corrected as shown below:

Title page,
Item [54], Title, reading "ADENOVIRAL VECTOR WITH A DELETION IN THE E1A CODING REGION EXPRESSING A HETOROLOGOUS PROTEIN," should read -- A METHOD OF INDUCING ANTIBODIES IN A MAMMAL USING A DEFECTIVE ADENOVIRUS ENCODING AN HBV S ANTIGEN --

Signed and Sealed this

Twenty-seventh Day of July, 2004

JON W. DUDAS
*Acting Director of the United States Patent and Trademark Office*